United States Patent [19]

Weber et al.

[11] Patent Number: 5,145,991
[45] Date of Patent: Sep. 8, 1992

[54] DISTYRYLBIPHENYL COMPOUNDS

[75] Inventors: Kurt Weber, Basel, Switzerland; Claude Eckhardt, Riedisheim, France

[73] Assignee: Ciba-Geigy Corporation, Ardsley, N.Y.

[21] Appl. No.: 701,299

[22] Filed: May 13, 1991

Related U.S. Application Data

[63] Continuation of Ser. No. 418,046, Oct. 6, 1989, abandoned.

[30] Foreign Application Priority Data

Oct. 13, 1988 [CH] Switzerland ............... 3829/88

[51] Int. Cl.[5] ............... C07C 309/32; C07C 604/46
[52] U.S. Cl. ............... 562/87; 544/107; 544/410; 546/184; 548/354; 548/579; 358/413; 562/83; 562/84
[58] Field of Search ............... 558/413; 562/83, 87, 562/84

[56] References Cited

U.S. PATENT DOCUMENTS

| | | | |
|---|---|---|---|
| 3,627,758 | 12/1971 | Weber et al. | 562/87 X |
| 3,849,485 | 11/1974 | Weber | 558/413 X |
| 3,956,395 | 5/1976 | Meyer | 558/413 X |
| 3,959,340 | 5/1976 | Weber | 558/413 |
| 3,980,713 | 9/1976 | Matsunaga et al. | 562/87 X |
| 3,984,399 | 10/1976 | Weber et al. | 558/413 X |
| 4,147,648 | 4/1979 | Gunter et al. | 562/83 X |
| 4,424,170 | 1/1984 | Weber | 562/83 |

FOREIGN PATENT DOCUMENTS

| | | | |
|---|---|---|---|
| 2226244 | 1/1973 | Fed. Rep. of Germany | 562/83 |
| 3013279 | 10/1981 | Fed. Rep. of Germany | 558/413 |

Primary Examiner—Richard L. Raymond
Attorney, Agent, or Firm—Marla J. Mathias; Edward McC. Roberts

[57] ABSTRACT

Distyrylbiphenyl compounds of formula

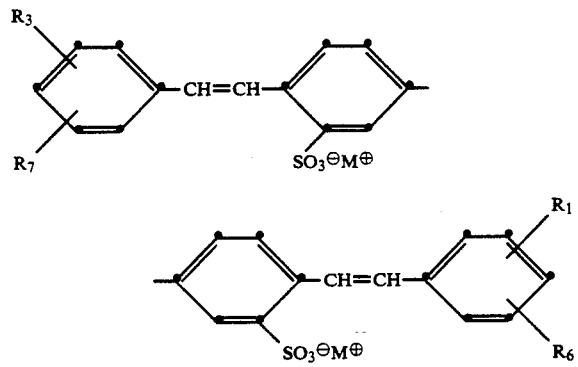

wherein $R_1$, $R_3$, $R_6$ and $R_7$ are halogen, hydrogen, $C_1$-$C_4$alkyl or cyano, and $M^\oplus$ is a salt-forming cation, are used as fluorescent whitening agents in solid and, preferably, liquid, detergent compositions. They are distinguished by good white effects and insignificant spotting behavior.

8 Claims, No Drawings

DISTYRYLBIPHENYL COMPOUNDS

This application is a continuation of application Ser. No. 418,046, filed Oct. 6, 1989, now abandoned.

The present invention relates to novel distyrylbiphenyl compounds, to their preparation, including novel intermediates, and to the use thereof.

It is commonly known to use fluorescent whitening agents in liquid detergent compositions. During treatment they exhaust on to the material to be washed and, by virtue of their special light absorption/emission properties, they effect a maintenance or enhancement of the original degree of whiteness.

This effect, however, is also responsible for the occurrence of bleach spots when textile fabric comes into direct contact with the liquid detergent composition, for example in a pretreatment. For this reason, the proposal is made in European patent application 167 205 to solve this problem by using specific stilbene triazolyl, stilbene triazine or distyrylbiphenyl fluorescent whitening agents.

Surprisingly, it has now been found that the formation of bleach spots can be prevented, while simultaneously achieving an excellent whitening effect, by novel compounds of formula

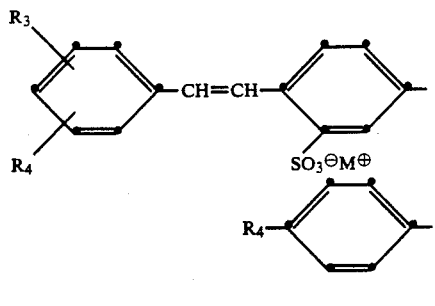
(I)

wherein
$R_1$ and $R_3$ are each independently of the other hydrogen, halogen, $C_1$-$C_4$-alkyl or cyano,
$R_2$ and $R_4$ are each independently of the other halogen, $C_1$-$C_4$alkyl or cyano, and
$M^\oplus$ is a salt-forming cation.

Suitable halogen substituents are in particular fluoro, chloro and bromo. Chloro is preferred.

Suitable $C_1$-$C_4$alkyl radicals are unbranched and branched alkyl radicals such as methyl, ethyl, n-propyl and isopropyl, n-, sec- and tert-butyl. These $C_1$-$C_4$alkyl radicals may in turn be substituted by, for example, aryl such as phenyl or naphthyl, $C_1$-$C_4$alkyl, $C_1$-$C_4$alkoxy, hydroxyl or cyano groups.

Illustrative of salt-forming cations $M^\oplus$ are alkali metal ions, ammonium ions or amine salt ions. Preferred amine salt ions are those of formula $H^\oplus NR_8R_9R_{10}$, wherein $R_8$, $R_9$ and $R_{10}$ are each independently of one another hydrogen, alkyl, alkenyl, hydroxyalkyl, cyanoalkyl, haloalkyl or phenylalkyl, or wherein $R_8$ and $R_9$, when taken together, complete a 5- to 7-membered saturated nitrogen-containing heterocycle which may additionally contain a nitrogen or oxygen atom as ring member, for example a piperidine, piperazine, pyrrolidine, imidazoline or morpholine ring, and $R_{10}$ is hydrogen.

Preferred distyrylbiphenyl compounds of formula I are those in which the cation $M^\oplus$ is an alkali metal ion, ammonium ion or amine ion, sodium and potassium being especially preferred for practical reasons.

Of particular interest are symmetrical compounds of formula I, and preferably those wherein $R_1$ and $R_3$ are hydrogen. Among these compounds, those in which $R_2$ and $R_4$ are $C_1$-$C_4$alkyl, preferably methyl, or chloro, merit special mention. Compounds of formula II

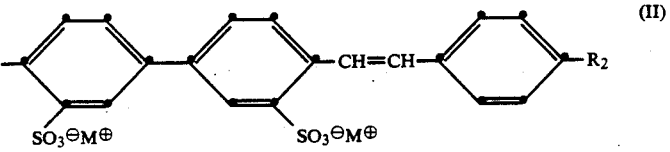
(II)

wherein $R_2$ and $R_4$ are as defined for formula I, are to be particularly highlighted.

Useful compounds are para-substituted compounds such as

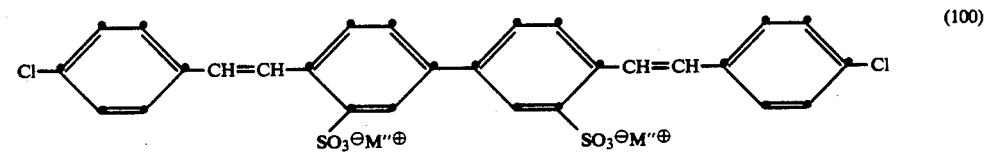
(100)

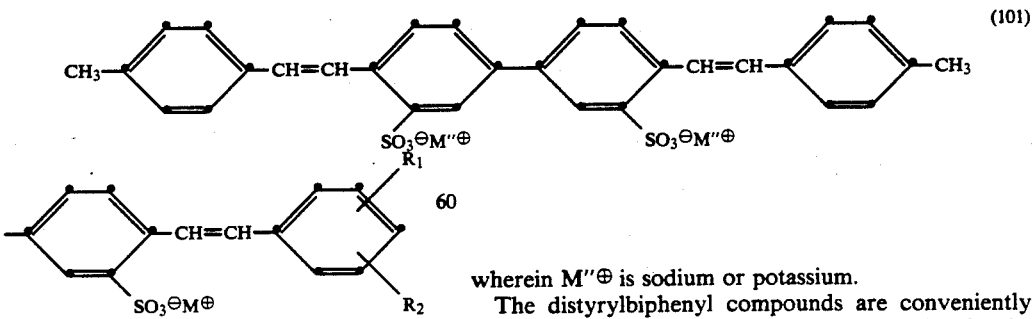
(101)

wherein $M''^\oplus$ is sodium or potassium.

The distyrylbiphenyl compounds are conveniently prepared by two routes (A or B), route A being for the preparation of symmetrical and unsymmetrical compounds, while route B is preferably followed for the preparation of the symmetrical compound.

A.

Compounds of formula I are obtained by starting from at least 1 mol of a compound of formula

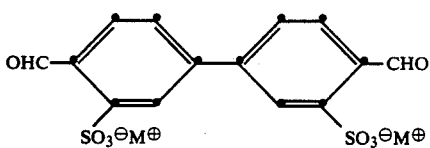
(X)

and 1 mol of a compound of formula

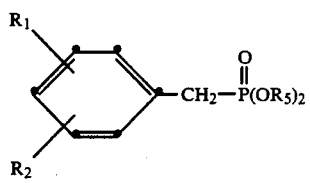
(XI)

as well as 1 mol of a compound of formula

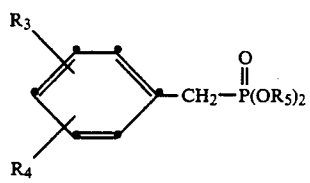
(XII)

and by carrying out the reaction in a polar solvent and in the presence of a strong base.

B.

In the presence of Pd/C, 2 mol of a compound of formula

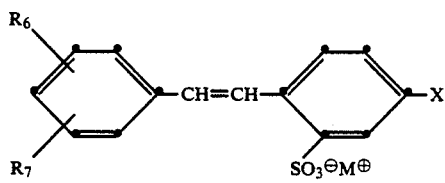
(XX)

are reacted with a base in a polar solvent to give symmetrical compounds of formula

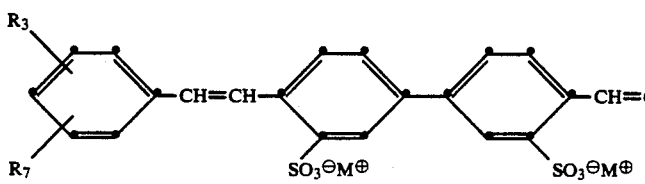
(III)

The starting stilbenes of formula (XX)

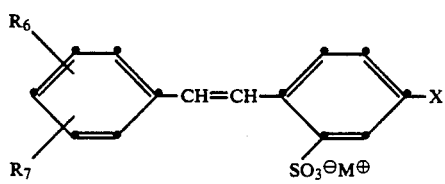
(XX)

wherein $R_6$ and $R_7$ are halogen, hydrogen, $C_1$-$C_4$alkyl or cyano, X is halogen and $M^\oplus$ is a salt-forming cation, excluding the compounds in which $R_6$ is hydrogen, $R_7$ is chloro in para-position to the stilbene radical and X is chloro, are novel.

Particularly important stilbenes of formula (XX) are those in which $M^\oplus$ is an alkali metal ion, an ammonium ion or an amine ion and, among these compounds, preferably those in which $M^\oplus$ is sodium or potassium.

In view of the reaction of (XX) to compounds of formula I, those compounds are preferred in which X is chloro.

Compounds of formula (XX), wherein $R_7$ is hydrogen, merit special mention.

Among the monosubstituted compounds of formula

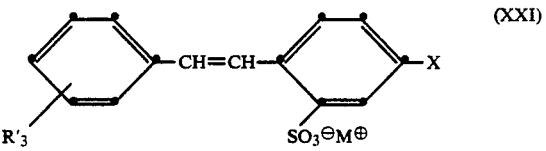
(XXI)

those in which $R_6'$ is $C_1$-$C_4$alkyl, preferably methyl, or cyano, are especially preferred.

Compounds of formula (XXI), wherein X is chloro, $R_6'$ is $C_1$-$C_4$alkyl and $M'^\oplus$ is an alkali metal ion, an ammonium ion or an amine ion, are of particular interest.

The compound of formula

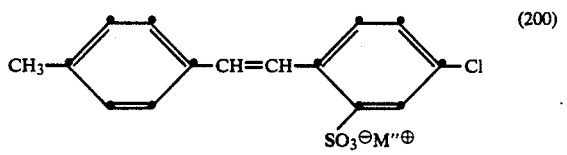
(200)

wherein $M''^\oplus$ is sodium or potassium, is particularly preferred.

The novel compounds of formula (XX) can be prepared in a manner known per se by reacting benzylphosphonates of formula

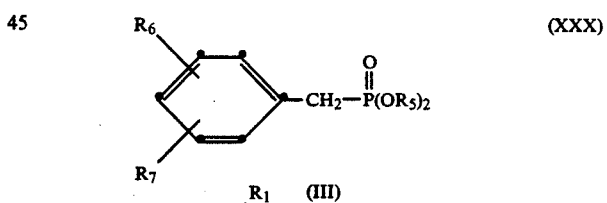
(XXX)

with aldehydes of formula

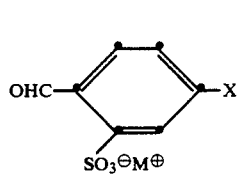

(XXXI)

in a polar solvent and in the presence of a strong base.

In the above formulae, $R_1$, $R_3$, $R_6$ and $R_7$ may be each independently of the other halogen, hydrogen, $C_1$-$C_4$alkyl or cyano, $R_2$ and $R_4$ may be each independently of the other halogen, $C_1$-$C_4$alkyl or cyano, $R_5$ is $C_1$-$C_4$alkyl, and X is halogen. The definitions given above apply in respect of $M^\oplus$, the possible halogens and the alkyl radicals.

Illustrative of suitable polar solvents are alcohols such as methanol, ethanol, isopropanol, butanol, glycols, glycol ethers such as 2-methoxyethanol, hexanols, cyclohexanol and cyclooctanol, and also ethers such as diisopropyl ether, tetrahydrofuran and dioxane, as well as dimethyl sulfoxide, formamide and N-methylpyrrolidone. Polar organic solvents such as dimethyl formamide and dimethyl sulfoxide are especially suitable. A number of the reactions can also be carried out in aqueous solution.

Suitable strong bases are especially the hydroxides, amides and alcoholates (preferably those of primary alcohols containing 1 to 4 carbon atoms) of alkali metals, those of lithium, sodium and potassium being of principal interest for economic reasons. In principle and in particular cases, however, it is also possible to use with success alkali metal sulfides and carbonates, aryl alkali compounds such as phenyllithium, or strongly basic amines (including ammonium bases), for example trialkylammonium hydroxides.

The temperature at which these reactions are carried out may vary within wide ranges. It is governed by α) the resistance of the solvent employed to the reactants, especially to the strongly basic alkali compounds, β) the reactivity of the condensation reactants, and γ) the efficacy of the combination of solvent/base as condensing agent.

In practice, therefore, temperatures in the range from ca. 10° to 100° C. are ordinarily suitable, especially if the solvent employed is dimethyl formamide or dimethyl sulfoxide. The preferred temperature range is from 20° to 70° C.

The compounds of formula I are used for whitening textile materials, in particular polyamides, wool and cotton, and paper.

A further utility is the preparation of detergent formulations—solid, gel-like and liquid. In this regard, the compounds of formula I are distinguished by very good white effects and a low spotting behaviour.

The washing powders of this invention contain, for example, the known mixtures of active detergents such as soaps in the form of chips, and powders, synthetics, soluble salts of sulfonic acid half-esters of higher fatty alcohols, of higher and/or polyalkylated arylsulfonic acids, sulfocarboxylates of medium to higher alcohols, fatty acid acylaminoalkyl or fatty acid aminoaryl glycerol sulfonates, phosphoric acid esters of fatty alcohols and the like. Suitable builders are, for example, alkali metal salts of carboxymethyl cellulose and other soil redeposition inhibitors, and also alkali metal silicates, alkali metal carbonates, alkali metal borates, alkali metal percarbonates, nitrilotriacetic acid, ethylenediaminetetraacetic acid, foam stabilisers such as alkanolamides of higher fatty acids. The detergents may further contain, for example, antistatic agents, superfatting skin protectants such as lanolin, microbicides, perfumes, and other fluorescent whitening agents, as well as bleaching agents such as perborate, singly or in conjunction with activators such as TAED, TAGU, NOBS and the like, or percarbonates or peracids, or photobleaching agents such as sulfonated zinc or aluminium phthalocyanines.

Washing powders of this invention contain, for example, 10-50% by weight of an anionic, nonionic, semipolar, ampholytic and/or zwitterionic surfactant, 0-80% by weight of a builder salt, 0-30% by weight of a bleach or bleaching system, and further optional conventional detergent components, for example those mentioned above.

Surfactants which the said washing powders may also suitably contain are water-soluble alkylbenzenesulfonates, alkyl sulfates, ethoxylated alkyl ether sulfates, paraffin sulfonates, α-olefin sulfonates, α-sulfocarboxylic acids and the salts and esters thereof, alkyl glyceryl ether sulfonates, fatty acid monoglyceride sulfates or sulfonates, alkylphenolpolyethoxy ether sulfates, 2-acyloxyalkanesulfonates, β-alkoxyalkanesulfonates, soaps, ethoxylated fatty alcohols, alkylphenols, polypropoxy glycols, polypropoxyethylenediamines, amine oxides, phosphine oxides, sulfoxides, aliphatic secondary and tertiary amines, aliphatic quaternary ammonium, phosphonium and sulfonium compounds, or mixtures of the cited substances.

Illustrative of alkaline builder salts which the washing powders may contain in an amount, for example, of 10-60% by weight are: water-soluble carbonates, borates, phosphates, polyphosphates, hydrogen-carbonates and silicates of alkali metals, water-soluble aminopolycarboxylates, phytates, polyphosphonates and polycarboxylates, as well as water-insoluble aluminium silicates.

The granular detergent formulation is conveniently prepared by spray drying.

Compounds of formula I, including the compounds in which $R_2$ and/or $R_4$ are hydrogen, are especially suitable for use as fluorescent whitening agents in liquid detergent compositions.

By liquid detergent compositions are meant the known and commercially available detergents disclosed, for example, in European patent application 167 205 or U.S. Pat. No. 4,507,219.

Preferably these liquid detergent compositions contain 1 to 60% of anionic, nonionic, zwitterionic and optionally cationic surfactants and 25 to 65%, preferably 40 to 55%, of water, in addition to 0.01-1%, preferably 0.05-0.2%, of a fluorescent whitening agent of formula III.

Specifically, the liquid detergent composition of this invention contains, in addition to the fluorescent whitening agent, 3 to 50%, preferably 15 to 25%, of anionic surfactants, 2 to 30%, preferably 4 to 15%, of nonionic surfactants, 3 to 30%, preferably 5 to 20%, of ethoxylated or non-ethoxylated $C_{10}$-$C_{14}$fatty acids such as capric, lauric, myristic, coconut and palm kernel fatty acid and mixtures thereof, 1 to 25%, preferably 1 to 10%, of detergent builders and, as optional components, 1 to 10%, preferably 1 to 5%, of zwitterionic surfactants, 0.5 to 3%, preferably 0.7 to 2%, of quaternary ammonium, amine or amine oxide surfactants, and 1 to 10% of conventional detergent ingredients such as enzymes, enzyme stabilisers, antioxidants, preservatives and bactericides, fragrances and dyes, complexing or sequestering agents, and solvents.

Useful surfactants are described, for example, in U.S. Pat. Nos. 4,285,841, 3,929,678 and 4,284,532 and in GB patent specification No. 2041986. It is particularly preferred to use the surfactants cited as preferred in European patent application 167 205. First foremost, however, the anionic surfactants used are non-ethoxylated or ethoxylated $C_{10}$–$C_{18}$alkyl sulfates, for example in the form of the triethanolamine salts, $C_{10}$–$C_{15}$alkylbenzene sulfonates or mixtures thereof, and the nonionic surfactants used are condensates of 1 mol of a $C_{10}$–$C_{15}$fatty alcohol with 3 to 8 mol of ethylene oxide.

Suitable detergent builders are the preferably polycarboxylated compounds cited in U.S. Pat. Nos. 4,321,165 and 4,284,532, for example citric acid.

When using compounds of formula

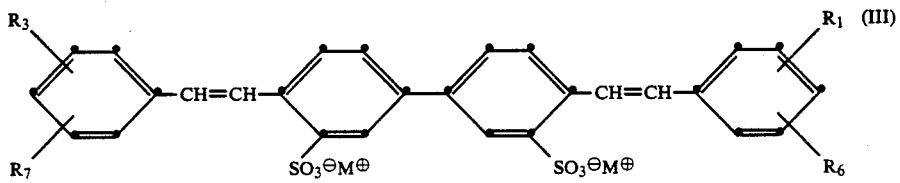

wherein $R_1$, $R_3$, $R_6$ and $R_7$ are each independently of the other halogen, hydrogen, $C_1$–$C_4$alkyl or cyano, and $M^\oplus$ is a salt-forming cation, the liquid detergent compositions are distinguished by excellent whitening properties, storage stability and low spotting behaviour.

Preferred distyrylbiphenyl compounds of formula III are those in which the cation $M^\oplus$ is an alkali metal ion, an ammonium ion or an amine ion, potassium and sodium being especially preferred for practical reasons.

Symmetrical compounds of formula III are of especial interest, preferably those in which $R_1$ and $R_3$ are hydrogen (VIa). Compounds meriting special mention are those in which $R_6$ and $R_7$ are $C_1$–$C_4$alkyl, preferably methyl, or chloro. Compounds of formula (IIa)

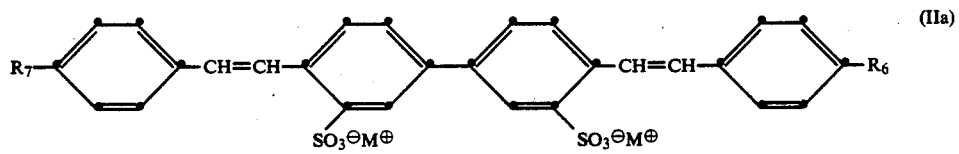

wherein $R_6$ and $R_7$ are as defined for formula III, are preferred.

Useful compounds are, for example, those of formula

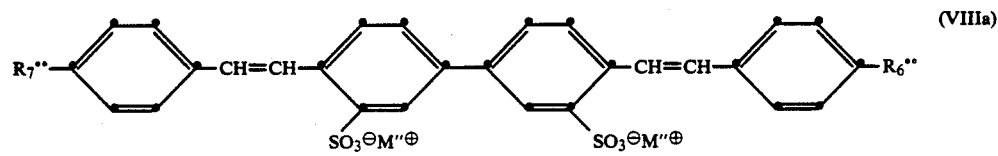

wherein $R_6^{\circ\circ}$ and $R_7^{\circ\circ}$ are chloro or methyl, and $M'''^\oplus$ is sodium or potassium.

The following Examples will serve to illustrate the invention. Parts and percentages therein are by weight. The spotting test is carried out as follows:

a) 0.1% (100% of active substance) of fluorescent whitening agent, or mixture of fluorescent whitening agents, is dissolved in a liquid detergent composition. 0.6 g of this detergent formulation (A) which contains a fluorescent whitening agent or mixture thereof is diluted with 400 ml of water (10°–12° German hardness) at a temperature of 30° C. (wash liquor B).

b) A piece of bleached cotton fabric (20 g) is clamped on a stenter frame.

c) 0.6 ml of detergent solution (A) is applied uniformly with a pipette to a premarked round area (5 cm diameter) of this cotton fabric which, after a treatment time of 30 seconds, is put into the prepared wash liquor (B), and washed for 15 minutes at 30° C. The cotton fabric is then rinsed with cold water and dried at 70° C.

d) The difference in the degree of whiteness according to Ganz between the treated area and the surrounding area is a criterion of the so-called spotting behaviour (formation of bleach spots) and is determined with a Zeiss RFC-3 photometer.

EXAMPLE 1

With stirring, 8.9 g of the potassium salt of 4,4'-bis-(formyl)-diphenyl-3,3'-disulfonic acid and 10.5 g of 1-diethylphosphonomethyl-4-chlorobenzene are charged at 40° C. to 120 ml of dimethyl formamide. Then 2.7 g of potassium hydroxide powder (89%) are added, and the mixture is heated to 65° C. and stirred for 4 hours. After cooling to room temperature, 120 ml of distilled water are added, and the reaction mixture is heated to 90° C. and clarified by filtration. The filtrate is cooled to room temperature and the crystallised product is filtered with suction. The filter product is recrystallised from a mixture of 50 ml of distilled water and 50 ml of dimethyl formamide and dried under vacuum, affording 1.5 g of the compound of formula

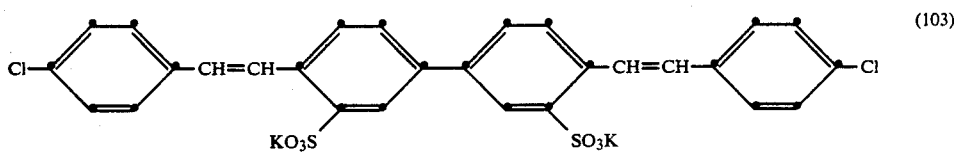
(103)

in the form of a greenish-yellow crystalline powder. UV spectrum: $\lambda_{max}=357$ nm, $\epsilon=69007$ (taken up in DMF/H$_2$O 1:1).

EXAMPLE 2

The following compounds can be obtained in accordance with the procedure of Example 1:

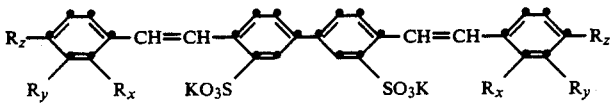

| No. | $R_x$ | $R_y$ | $R_z$ | UV (DMF/H$_2$O 1:1) $\lambda_{max}$ (nm) | $\epsilon$ |
|---|---|---|---|---|---|
| (104) | H | CN | H | 353 | 73 376 |
| (105) | CN | H | H | 353 | 56 880 |
| (106) | CH$_3$ | H | H | 353 | 63 207 |
| (107) | H | Cl | H | 353 | 66 292 |
| (108) | H | Cl | Cl | 357 | 69 630 |
| (109) | Cl | H | Cl | 356 | 70 418 |

EXAMPLE 3

With stirring and excluding air, a suspension of 2.7 g (0.007 mol) of the sodium salt of 4,4'-bis(formyl)-diphenyl-3,3'-disulfonic acid and 2.96 g (0.012 mol) of 1-diethylphosphonomethylbenzene are added over 5 minutes to a suspension of 13.2 g of potassium hydroxide powder (89%) in 40 ml of dimethyl formamide. The reaction mixture is stirred for 5 hours at 40°–45° C. and poured into 350 ml of distilled water of 70° C. To this solution are added 150 g of sodium chloride and 150 g of ice and the batch is stirred overnight, then filtered with suction. The filter cake is washed with 500 ml of 20% brine and dissolved hot in 140 ml of distilled water. The solution is treated with 2 g of activated carbon, filtered, and the filtrate is allowed to crystallise. The crystalline product is filtered with suction and vacuum dried at 80°–85° C., affording 0.23 g of the compound of formula

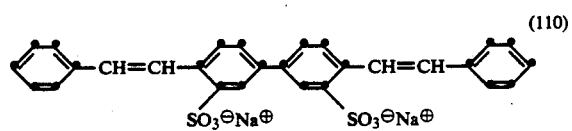
(110)

in the form of a pale yellow crystalline powder. Melting point: >300° C.

EXAMPLE 4

With stirring, 45.6 g (0.12 mol) of the potassium salt of 4-chlorobenzaldehyde-2-sulfonic acid (70%) and 30.5 g (0.12 mol) of 1-diethyl-phosphonomethyl-4-methylbenzene are charged at 40° C. to 300 ml of dimethyl formamide. Then 12.5 g of potassium hydroxide are added and the reaction mixture is stirred for 15 hours at 40° C. After addition of 350 ml of water, the reaction mixture is neutralised with acetic acid and clarified by filtration. The filtrate is evaporated to dryness and the residue is recrystallised from 200 ml of water, affording 27 g of the compound of formula

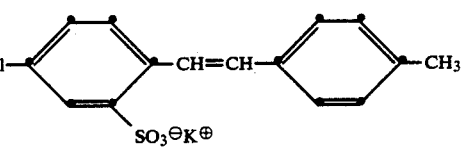
(201)

in the form of a white crystalline powder. Melting point: >300° C.

EXAMPLE 5

With stirring, 17.3 g (0.05 mol) of the potassium salt of 4-chloro-4'-methylstilbene-2-sulfonic acid according to Example 4 and 2.8 g of potassium hydroxide are dissolved in 200 ml of deionised water. After addition of 1 g of 5% Pd/C, 80.4 ml of a 1:1 mixture of methanol and water are added dropwise, and the reaction mixture is thereafter stirred for 15 hours at 85°–90° C. After clarifying filtration using a filter aid, the reaction mixture is evaporated to dryness. The crude product is chromatographed over a silica-gel-column of 11.5 cm diameter, using as eluant 100 parts by volume of isopropanol+35 parts by volume of toluene+20 parts by volume of ammonia (25%) and 100 parts by volume of methyl cellosolve+80 parts by volume of deionised water+20 parts of ammonia (25%). The yellow product so obtained is crystallised from 250 ml of water+50 ml of methyl cellosolve, with the addition of a small amount of potassium hydroxide and activated carbon. The crystalline product is dried under vacuum at 110° C. to give 1.5 g of the compound of formula

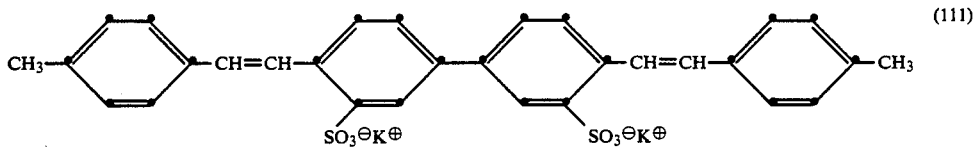

(111)

in the form of a yellow crystalline powder. Melting point: >300° C.

EXAMPLE 6

To a pulp of 100 parts of cellulose in a hollander are added 2 parts of resin size. After 10 minutes, 0.2 part of the compound of Example 5, dissolved in 20 parts of water, is added first, followed by the addition 15 minutes later of 3 parts of aluminium sulfate. The treated pulp is then transferred from a mixing chest to a paper machine on which the paper is manufactured in known manner. The paper so obtained has an excellent white effect.

EXAMPLE 7

100 parts of cotton are treated at a liquor to goods ratio of 1:20 for 20 minutes at 60° C. in a bath containing 0.1 part of the compound of Example 5 and 2.5 g/l of Glauber's salt and to which a further 2.5 g/l of Glauber's salt are added after 5 minutes. The goods are then rinsed and dried. A strong white effect is obtained.

EXAMPLE 8

1 g of the compound of Example 5 is dissolved in 1 liter of soft water which contains 2 g of polyphosphate and 5 ml of 80% acetic acid. A piece of polyamide 6 (Perlon ®) tricot) is padded cold with this bath to a pick-up of 110% and then thermoset for 40 seconds at 190° C. The textile material has an excellent white effect after this treatment.

EXAMPLE 9

100 parts of polyamide 66 (nylon tricot) are treated at a liquor to goods ratio of 1:20 in soft water which contains 0.1 part of the compound of Example 5, 3 g/l of stabilised hydrosulfite and 1 ml/l of 80% acetic acid. The bath is heated over 30 minutes from 40° C. to 98° C. After 30 minutes at 98° C., the bath is cooled to 40° C. over 15 minutes and the goods are rinsed in cold water and dried in a drying cabinet at 60° C. An excellent and brilliant white effect is obtained.

EXAMPLE 10

A granular detergent formulation having a residual moisture content of ca. 5% is prepared by spray drying a slurry consisting of 1 part of water and 1 part of a detergent of the following composition:
8.4 g of linear dodecylbenzenesulfonate,
3.1 g of tallow alcohol tetradecane ethylene glycol ether (14 mol of EO),
3.7 g of sodium soap (mainly of behenic acid and $C_{14}$-$C_{20}$acids),
45.8 g of sodium triphosphate,
7.9 g of sodium silicate,
2.0 g of magnesium silicate,
1.2 g of carboxymethyl cellulose,
0.2 g of ethylenediaminetetraacetate,
22.2 g of sodium sulfate,
0.1 g of the compound of formula 5.

4 parts of this granular formulation are dissolved in 1000 parts of water of 12° German hardness at a temperature of 40° C. Five pieces of bleached cotton (each equivalent to 10 parts) are washed in his bath at 40° C. for 15 minutes, then rinsed under cold running water and centrifuged for 30 seconds in a tumbler at a speed of ca. 1000 rpm. This washing procedure is carried out 3 times, then the cotton pieces are dried and the degree of whiteness is determined by the method of Ganz, using a Zeiss RFC 3 photometer.

Very good white effects in the order of magnitude of 200 units are obtained.

EXAMPLE 11

The spotting test is carried out with a fluorescent whitening agent of formula

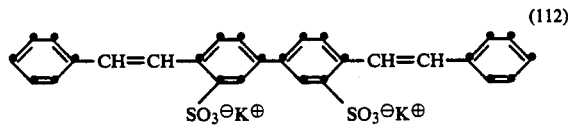

(112)

and a liquid detergent composition comprising
15 parts of $C_{11}$-$C_{13}$alkylbenzenesulfonate,
14 parts of $C_{14}$-$C_{15}$polyethoxy fatty alcohol (7 mol of ethylene oxide),
10 parts of soap,
9 parts of ethanol,
4 parts of sodium citrate,
5 parts of triethanolamine,
43 parts of water.

The 0.1 part of the fluorescent whitening agent can be readily incorporated into this formulation as a clear, stable solution which is stable for several months.

The spotting test shows only an insignificant formation of bleach spots, although 0.1 part of the cited fluorescent whitening agent incorporated in the above detergent gives very good white effects in wash tests, even at low wash temperatures. When, for example, bleached cotton is washed with 3 g of the above detergent per liter of wash liquor at a liquor to goods ratio of 1:20 and a temperature of 30° C. for 15 minutes, degrees of whiteness (measured spectrophotometrically by the method of Ganz) of ca. 140 after the first wash or ca. 175 after 5 wash cycles, are obtained.

EXAMPLE 12

The procedure of Example 11 is repeated, replacing the fluorescent whitening agent used therein by that of Example 5. White effects of ca. 150 are obtained after the first wash, of ca. 195 after the fifth wash at 30° C., or of ca. 155 after the first and ca. 195 after the fifth wash, at a wash temperature of 60° C., as well as a still more insignificant formation of bleach spots.

Even if in each wash cycle the cotton is dried in daylight up to 200 Langley (equivalent to drying outdoors in European regions), only a very insignificant and scarcely visible loss in whiteness compared with the non-exposed sample is observed.

What is claimed is:

1. A distyrylbiphenyl compound of formula

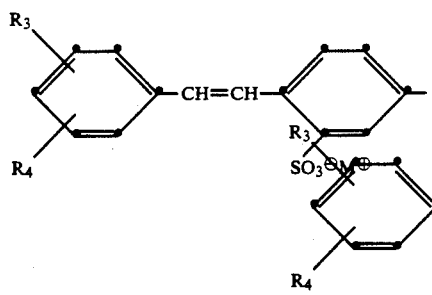

(I)

wherein
R₁ and R₃ are each independently of the other hydrogen, $C_1$–$C_4$-alkyl or cyano,
R₂ and R₄ are each independently of the other $C_1$–$C_4$alkyl or cyano, and M⊕ is a salt-forming cation.

2. A distyrylbiphenyl compound according to claim 1 which is symmetrical.

3. A distyrylbiphenyl compound according to claim 1 of formula

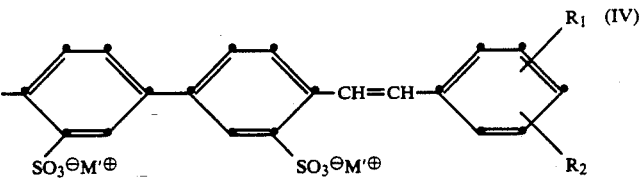

(IV)

wherein M'⊕ is an alkali metal ion, an ammonium ion or an amine ion, and R₁ to R₄ are as defined in claim 1.

4. A distyrylbiphenyl compound according to claim 1 of formula

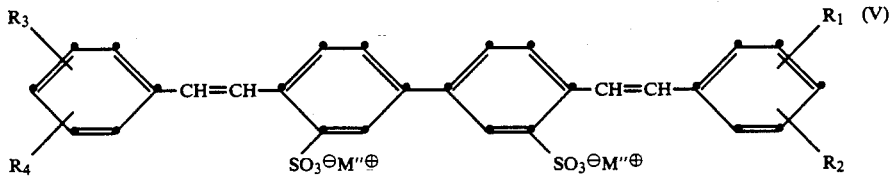

(V)

wherein M''⊕ is sodium or potassium, and R₁ to R₄ are as defined in claim 1.

5. A distyrylbiphenyl compound according to claim 1 of formula

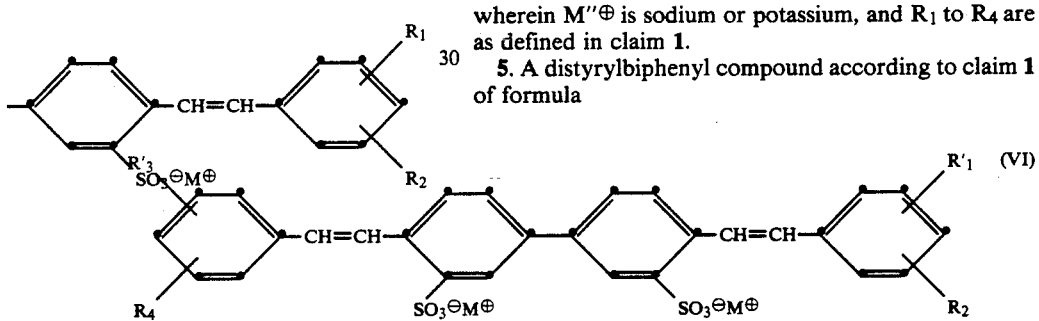

(VI)

wherein R'₁ and R'₃ are hydrogen, and R₂, R₄ and M⊕ are as defined in claim 1.

6. A distyrylbiphenyl compound according to claim 1 of formula

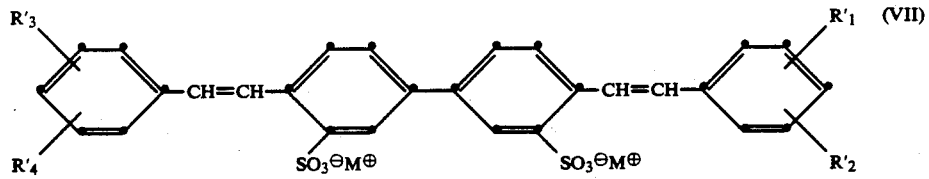

(VII)

wherein R'₂ and R'₄ are $C_1$–$C_4$alkyl, R'₁ and R'₃ are hydrogen, and M⊕ is a salt-forming cation.

7. A distyrylbiphenyl compound according to claim 1 of formula

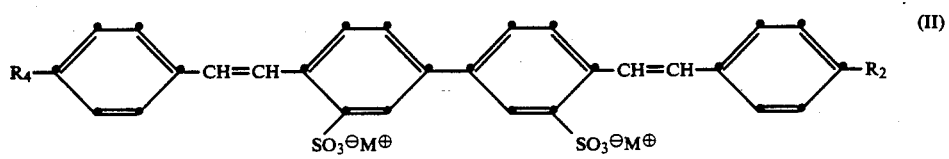

(II)

wherein R₂, R₄ and M⊕ are as defined in claim 1.

8. A distyrylbiphenyl compound of formula

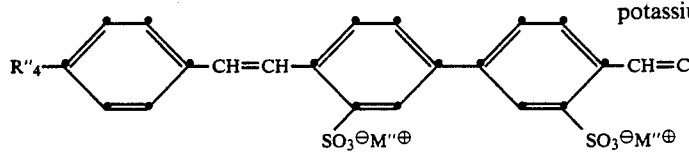
wherein $R''_2$ and $R''_4$ are methyl, and $M''^\oplus$ is sodium or potassium.